United States Patent [19]

Johnson

[11] 4,295,200
[45] Oct. 13, 1981

[54] AUTOMATIC PARTICLE ANALYZING SYSTEM

[75] Inventor: Richard F. Johnson, Vero Beach, Fla.

[73] Assignee: The United States of America as represented by the Secretary of the Navy, Washington, D.C.

[21] Appl. No.: 90,787

[22] Filed: Nov. 2, 1979

[51] Int. Cl.³ .......................................... G01N 15/02
[52] U.S. Cl. ................................ 364/555; 364/525; 250/204; 356/335
[58] Field of Search ............... 364/555, 525; 356/36, 356/335; 350/46; 250/204

[56] References Cited

U.S. PATENT DOCUMENTS

| | | | |
|---|---|---|---|
| 3,922,532 | 11/1975 | Kitchener et al. | 364/555 |
| 3,932,733 | 1/1976 | Olsen et al. | 364/525 X |
| 3,973,725 | 8/1976 | Watanabe et al. | 364/555 X |
| 3,984,678 | 10/1976 | Uchiyama et al. | 350/46 X |
| 4,021,117 | 5/1977 | Gohde et al. | 356/335 X |
| 4,135,821 | 1/1979 | Pechin et al. | 356/335 |
| 4,174,892 | 11/1979 | Osawa | 250/204 X |
| 4,203,031 | 5/1980 | Kamachi et al. | 250/204 X |
| 4,206,650 | 6/1980 | Berber et al. | 356/36 X |
| 4,207,001 | 6/1980 | Lynch et al. | 356/335 |

Primary Examiner—Edward J. Wise
Attorney, Agent, or Firm—Richard S. Sciascia; Thomas M. Phillips

[57] ABSTRACT

A measured stream of particles is dropped onto the apex of a distributor cone where it is divided into a circular pattern falling through a narrow sizing zone onto the peripheral edge of a rotatable platen. Platen rotation carries each particle into a frame area viewed, preferably, by a microscope and a TV camera the output of which is applied to a computer programmed to analyze selected characteristics. A rotatably-indexed mirror system reflects selected views into the microscope for the analysis. Interfaced with the computer is a signal generator providing feed-back signals that synchronously control system operation. For example, a feed-back signal stops platen rotation when a particle is brought into the viewing or frame area. Other signals control other functions such as the indexing of the mirror system to provide the desired views, i.e. front, back, top, bottom, etc. Scanning devices other than optics can be used if so desired.

14 Claims, 8 Drawing Figures

AUTOMATIC PARTICLE ANALYZING SYSTEM

BACKGROUND OF THE INVENTION

The invention relates to systems for analyzing and sorting particles according to selected characteristics.

Systems for sorting various types of particulate matter are well-known and have been used commercially for a variety of purposes such as quality control in the final inspection of grains and other free-flowing granular products. Their function, primarily, is to sort out and remove foreign or non-conforming material from the final product. To achieve this end, a combination of mechanical, optical, electronic and pneumatic components somewhat comparable to the components used in the present system usually are employed.

In other respects, however, they differ significantly from the present system. Thus, as will be described, the present system is concerned more directly with a relatively detailed and sophisticated analysis of each individual particle rather than with the somewhat cursory procedures used for quality control. For example, one of its primary uses is in the field of micropaleontology where a fairly large and varied amount of data must be obtained for each particle. In particular, it has been used for a rather voluminous study of the shell structures of foraminafera, although a wide variety of other uses clearly is contemplated. Quality control machines, in contrast, are designed to rather quickly distinguish the 'good' from the 'bad' according to one or two easily and simply determined characteristics. Their emphasis is upon speed or high handling rates and, to achieve this end, it is customary to examine and sort the particles as they are moved in a flowing stream past a viewing system which receives light reflected from the particles and passes it to detectors such as photomultipliers or the like.

In the present system, the emphasis instead is upon a programmed and relatively detailed 'look' at each particle and such a 'look' cannot be obtained if the particles are moving in a steady flow past the viewer. Each particle, therefore, is stopped for the examination. Further, each must be stopped in a precise position which permits the viewing mechanism to be finely focussed and also, preferably, in a position in which the particles can be viewed from several different angles needed to analyze different characteristics. In the present system, therefore, such matters as particle feed and handling which must be precise, reliable and efficient. Also, it is concerned with a complete automation of the handling as well as the anaylsis itself so as to provide a system that can operate unattended for the long periods of time needed to obtain the rather voluminous data needed for the study. As will be described, computer technology presently is using both to control and to synchronize all of the mechanical aspects of the system as well as the particle analysis. As far as is known, prior art systems have not employed comparable controls or, in fact, comparable handling and viewing mechanisms.

BRIEF DESCRIPTION OF THE DRAWINGS

The present invention is illustrated in the accompanying drawings of which.

DETAILED DESCRIPTION OF THE INVENTION

Figure 1:
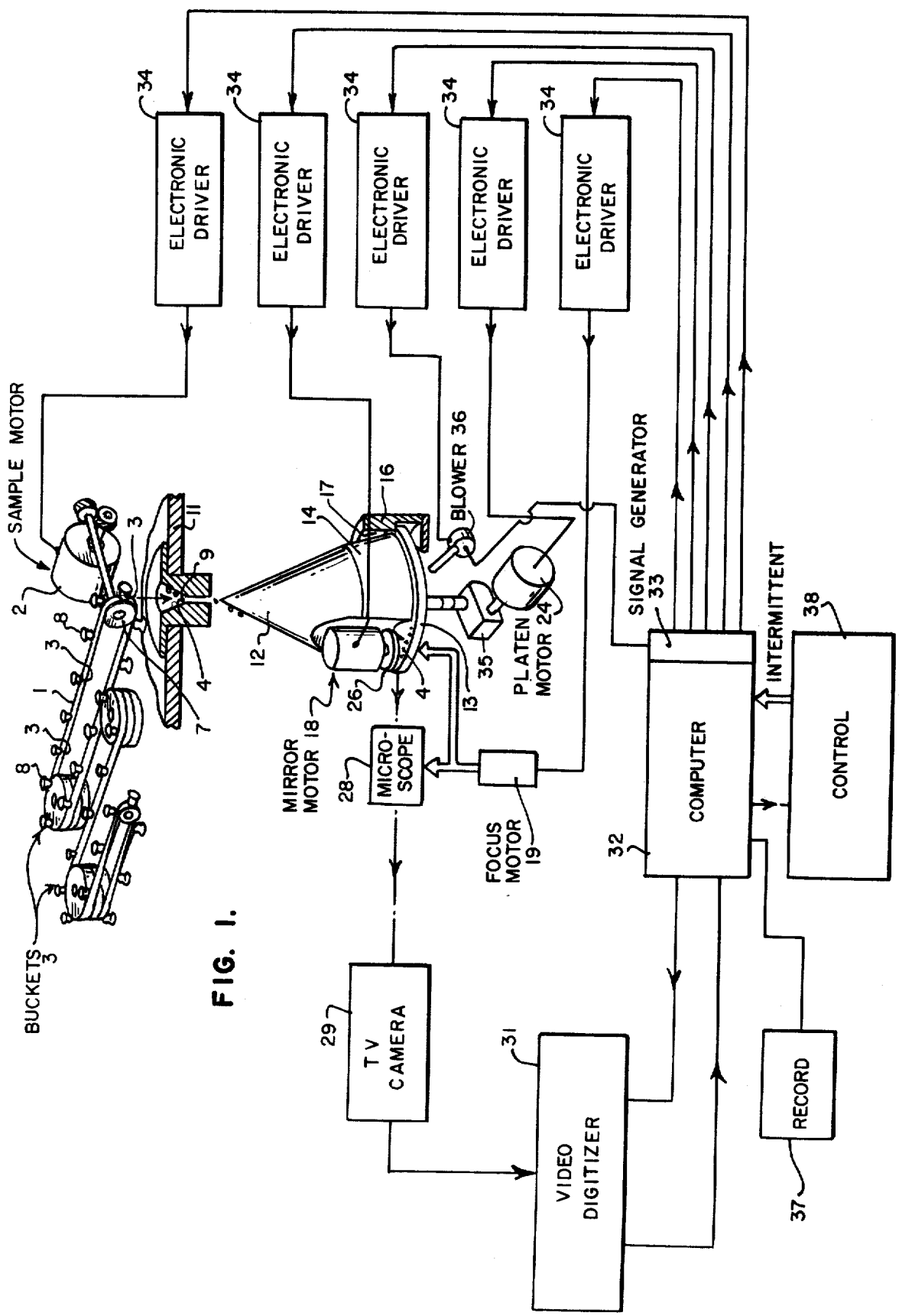
FIG. 1 is a schematic view showing the various mechanical, optical and electronic components of the system and their operative interrelationships.

Referring to FIG. 1, an endless conveyor belt or chain 1 driven by a motor 2 carries a plurality of relatively small sample cups 3 each filled with a supply of free-flowing particles 4 such as the foraminafera shells which, as already noted, have been the subject of a present study. Motor 2, preferably, is a stepped motor used to advance the cups incrementally and, as will be noted, the advance includes a loop 6 formed around a sprocket. Each cup then must travel around the loop and, in so doing, the incremental or stepped advance progressively tips the cup a certain amount sufficient to spill a small supply of samples over its flared lip portion 8 into a delivery funnel 9. This operation is shown in more detail in FIG. 2. Funnel 9, as well as the conveyor and its motor are carried by a stationary frame structure including a horizontal plate 11.

Figure 2:
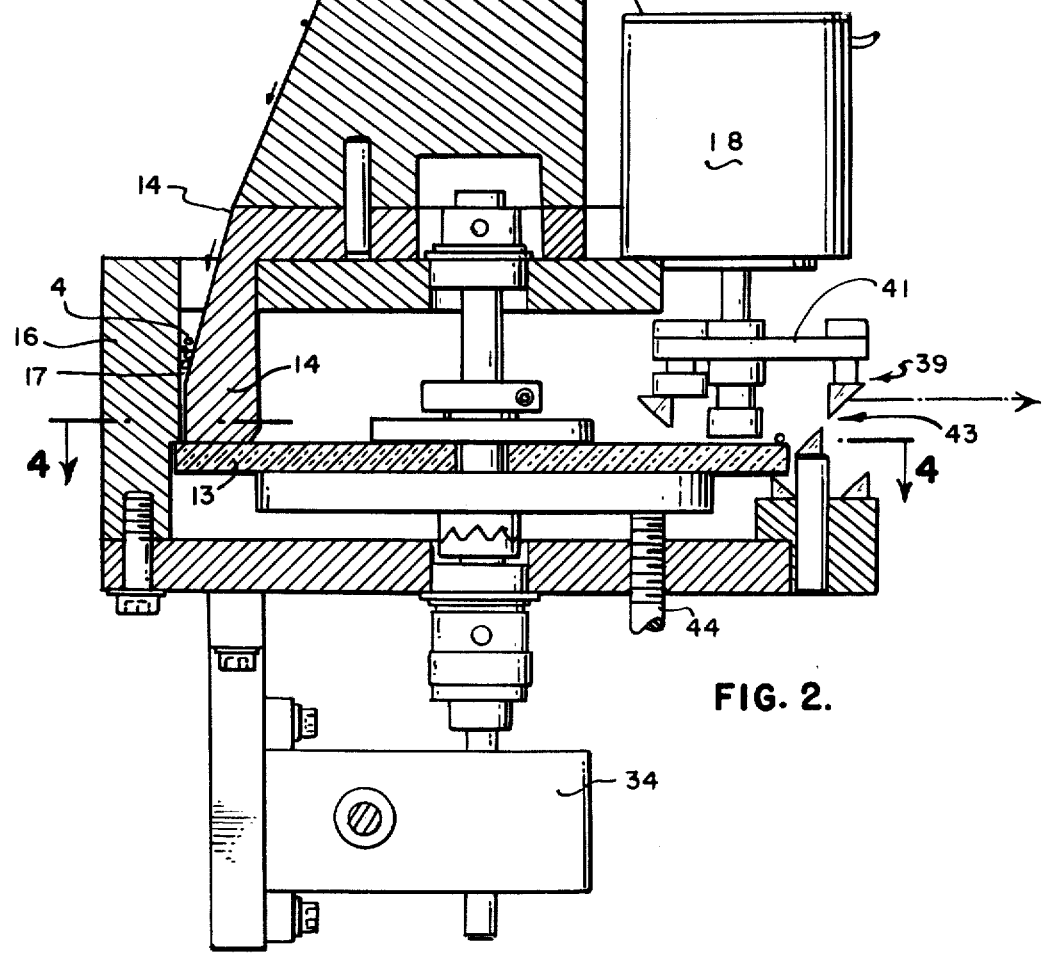
FIG. 2 is another somewhat schematic view in partial section showing in some detail a particular particle feeding and handling arrangement.
Figure 4:
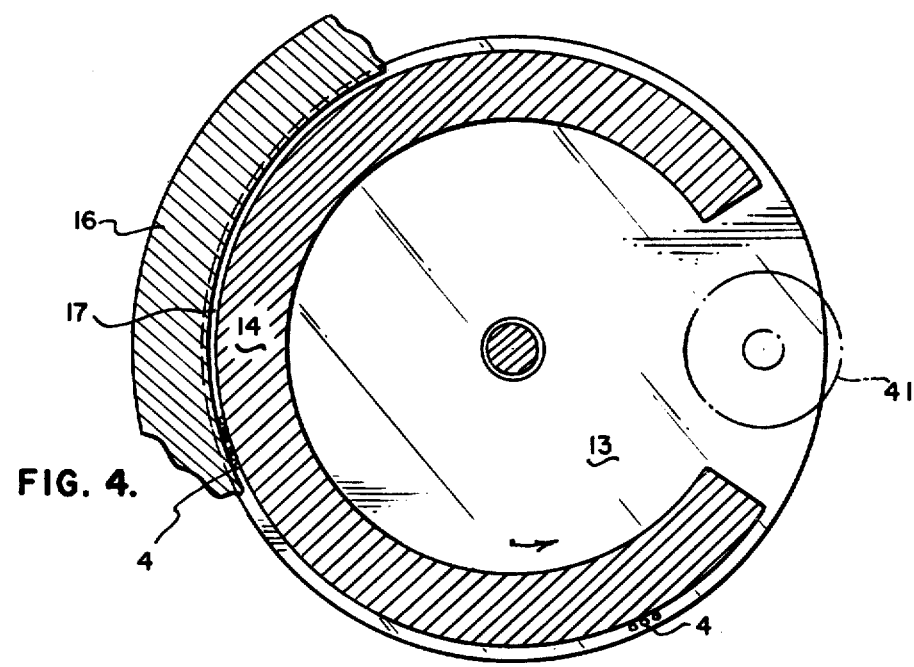
FIG. 4 is a sectional view taken along lines 4—4 of FIG. 2.

The samples spilling from the cups fall in a narrow stream onto the apex of a distributor cone 12 used to divide the stream into a circular pattern for delivery to and deposit on a rotatable wheel-like platen 13. For reasons that will become apparent, the particle specimens are deposited in a narrow, preferably single file, line circumferentially on the peripheral edge of platen 13 and the splitting or distributor cone, as well as a sizing plate 14, are used to achieve this desired disposition. Specifically, particles 4 fall in their circular pattern from cone 13 onto the surface of sizing plate 14 which, as best seen in FIG. 2, is surrounded by a circular main frame plate member 16 spaced from the sizing plate a predetermined amount to provide a small sizing zone or feed aperature 17. Functionally, the feed aperature is sized to restrict the width of the opening through which the particles drop onto the platen and this restriction narrows the line of the particles formed on the periphery of the platen. Narrowness, in turn, facilitates and improves the viewing of the particles by the optical components to be described. In particular, the narrowness of the line is a factor in determining the width of the frame size or field viewed by the optics of the present system. As is true in most optical viewing systems, a small or narrow field accentuates the optical image of a particle lying within it.

It should be noted at this point that, in actual form, cone 12 and sizing plate 14 are not geometrically circular. Instead, their circular contour is broken to permit the mounting of a mirror motor 18 the function of which will be subsequently considered. The break is for the purpose of increasing the compactness of the component arrangement. It has some disadvantage in that it permits a few of the particles to fall onto more central portions of the platen, but, in the particular examination for which the illustrated apparatus has been specially adapted, this has not been a matter of significant concern. In other studies or applications, it may be desirable to rearrange the mirror motor to preserve the full circular geometry of the cone and plate.

As has been noted platen 13 is rotatable and its rotation obviously is for the purpose of carrying the deposited particles into position for optical examination. During the feeding operation, however, the platen is stationary. Also, in feeding particles to the platen, the thinness of the line formed on its periphery can be improved by a special manupulation of the platen. Specifically, at the time that the particles are being fed to the sizing plate aperature, platen 13 is raised to bring it into actual contact with the bottom surface of the sizing plate. This contact, of course, blocks the flow and causes the aperature to fill with a small supply of particles. When filled or partially-filled, platen 13 then is moved downwardly away from the sizing plate and the particles drop a short distance one by one onto the platen.

Figure 3:
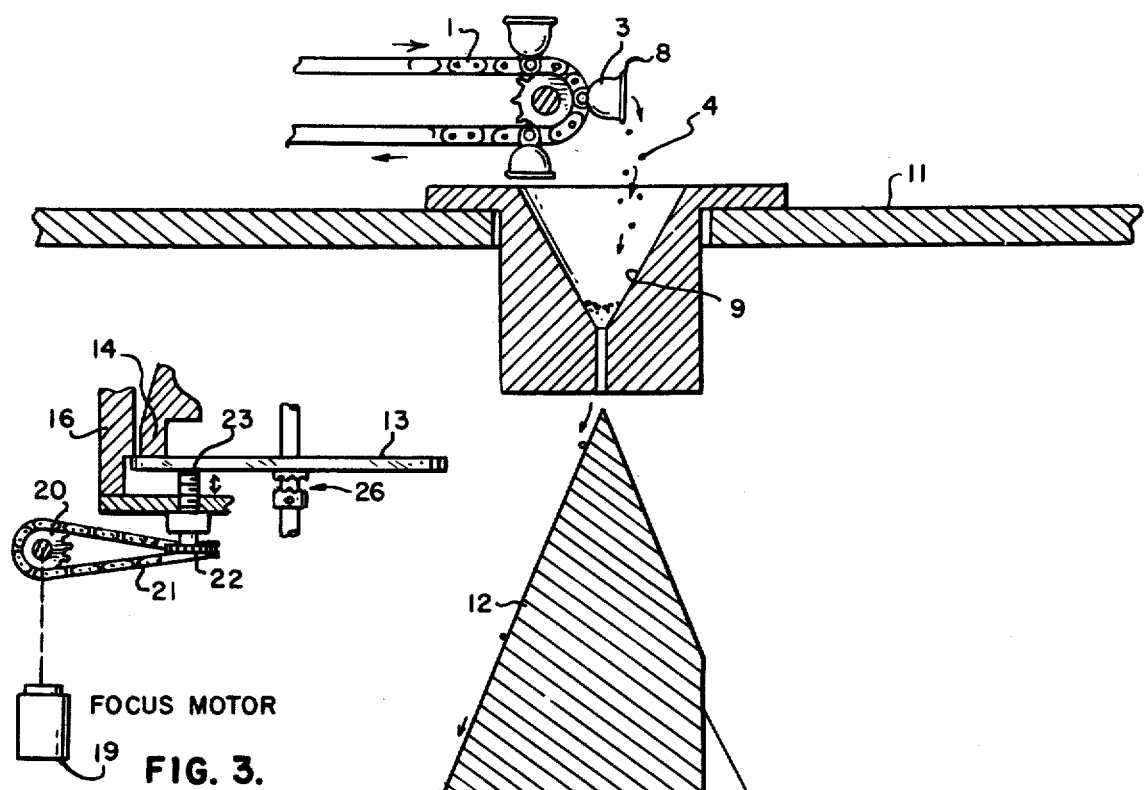
FIG. 3 illustrates a focussing arrangement used in the system.

The manner in which the platen is moved is illustrated in FIG. 3. As shown, it is under the control of a so-called focus motor 19 used to drive a sprocket 20 and rotate a belt 21 and a second sprocket 22. The rotation is applied to a threaded screw 23 contacting the underside of platen 13 to rais and lower the platen. To permit the platen rotation needed for particle transport, screw 23 moves out of contact with the sizing plate. Also, the rotational drive of the platen which, as shown, is derived from a platen motor 24, is coupled through a meshing tooth arrangement 26 (FIG. 3) both to permit the platen to be raised and to recouple the drive when lowered.

As has been noted, the platen is rotated to carry deposited particles one-by-one into a position in which they can be viewed and their characteristics analyzed. This position known as a framing zone is the area viewed by a special mirror system 27 (FIG. 2) functioning in a manner to be described to reflect different aspects of the positioned particles into a microscope 28. A TV camera 29, in turn, scans the microscope and provides a video output coupled through a digitizer 31 for application in digital format to a programmed general purpose computer 32.

Interfaced with the computer is a signal generator 33 functioning responsively to the digitized video input and to the computer program, to generate control signals which, as shown, are applied to a plurality of electronic drivers 34. These drivers which, in effect, are electronic switches, operate in a conventional manner to control the power for the various motors which already have been identified. Thus, as shown in FIG. 1, one driver controls platen rotating motor 24 which, as shown, is coupled to the platen through a speed reducer 35. In other words, the power that drives the motor is switched to cause the platen either to rotate or to stop. The other drivers control conveyor motor 2, mirror motor 18 and focus motor 19. As also will be noted, a blower 36 is coupled to the signal generator through yet another driver. The operation of this blower will be considered subsequently.

Computer 32 has the combined function of controlling and synchronizing the mechanical operations of the system components and of analyzing the digital input derived from the scans of the particles brought into the framing or viewing area. Most suitably, the data is recorded in digital form in a recorder 37. Also, computer operation can be controlled by an operator from a console 38. For example, in the system used in the particular foraminafera study, the computer is optionally controlled to actually draw or trace the shape of each particle. Since this tracing step takes a significant amount of time, it has been used selectively.

Figure 5:
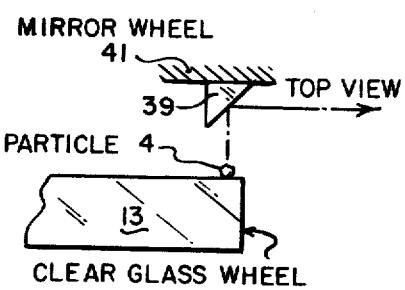
FIGS. 5, 6, 7 and 8 illustrate the operation of a mirror system used to obtain different views of the particle being examined.
Figure 6:
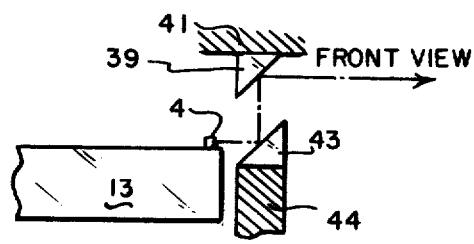
Figure 7:
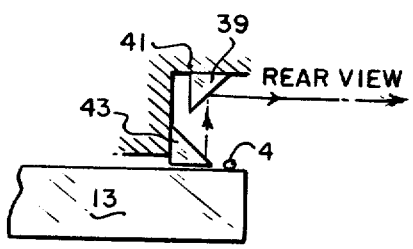
Figure 8:
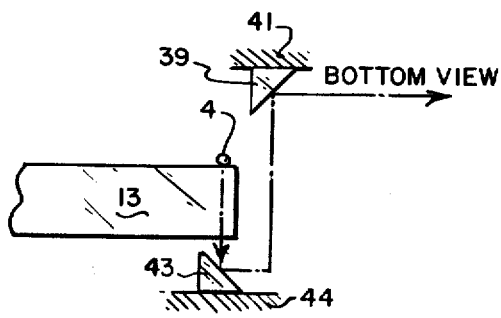

Mirror system 27 shown in FIG. 2 and its operation illustrated in FIGS. 5-8. Its main purpose is to provide different views of the particles such, for example, as front, rear, top and bottom views. These different views then are analyzed successively by the computer which is programmed to examine such particular points or aspects of the particles as may be desired. To obtain the different views, the mirror system includes a first plurality or set of reflective members or mirrors 39 mounted on a mirror wheel 41 which, as shown, is rotatably indexed by motor 18. Also, another set or plurality of mirrors 43 is mounted in fixed positions on a stationary center plate 44 which is a part of the systems supporting frame. Functionally considered, the different views are obtained by rotatably indexing the mirror wheel. Depending upon the rotated position of the wheel, one of its set of mirrors 39 cooperates with one of the fixed mirror 43 to reflect a particular view into microscope 28 or into whatever other optical viewer may be used in place of the microscope. For example, as shown in FIG. 5, the mirror wheel has been rotated to such a position that one of its reflecting members 39 'looks' at the top of the particle to provide a top view. In FIG. 6, wheel rotation has indexed a reflecting member 39 into position to receive the reflection of the particle from a fixed mirror 43 which, as shown, 'looks' at the front of the particle. Since mirror 43 is fixed, it always 'looks' at the particles but the front view is not transmitted to the microscope until the wheel is indexed into the FIG. 6 position. Similarly, rear and top views are obtained in the manner shown in FIGS. 7 and 8. To obtain the FIG. 8 bottom view, it will be noted that the platen must be a transparent member to permit fixed reflector 43 to see the particle through the platen. Obviously, the precise positioning of the mirrors is a design consideration which easily can be worked out for any particular application. Also, if desired, the arrangement can be designed to provide views other than those which have been described.

Before considering the operation of the system as a whole, it may be helpful to further identify its various components. First, it should be recognized that all of the optical, electronic, electrical and pneumatic components are standard items available on the commercial market. For example, all motors, except that of the blower, are commercial Superior Electric M062-F009 motors and all of the electric drivers are Superior Electric STM103. Others, of course, can be substituted. Blower 36 simply is a conventional air blower with its own motor.

As to the optical system, the arrangement used in the foraminafera study included a Wild M5 microscope, an RCA TC 1005/01 TV camera and a Colorado Video Model 270 video digitizer. Again, other units can be used and, in fact, as far as the present invention is concerned other scanning systems can be substituted. The microscope, for example, has been needed in the present implementation but, in others, it might not be. Also, the term TV camera is intended in its broad sense to include any comparable device capable of converting an optical input into a video signal output.

Computer 32, in the illustrated implementation, is a commercially-available general purpose computer known as the HP21005 microcomputer which comes with a writeable control store. Signal generator 33, as probably is apparent, is an interfaced component or chip normally associated with microcomputers. It has been specially identified in the foregoing description primarily because of its significant role in applying what amounts to a computer feed-back for the purpose of controlling and synchronizing the mechanics of the system, i.e. the feed, platen rotation, mirror wheel rotation, focussing and blower operation. Aside from this important function, it is a standard well-known component.

Programming of the computer, of course, is of critical concern in the actual implementation and use of the system. However, the particular manner in which it is programmed for the actual examination of the particle characteristics is not considered part of the present invention. For example, in the foraminafera study, it was programmed to scan 23,000 points evenly distributed in the TV frame. If desired, however, it could scan all 245,760 points in the frame although such a detailed scanning would take 2 seconds on the Model 270 digitizer. Clearly, the scanning detail of other examinations could be drastically limited with a considerable speeding-up of the entire operation.

It also will be recognized that the programming must include a sequence of instructions controlling the generation of the signals used to energize and deenergize the various motors at appropriate intervals. Again, such programming is standard procedure which should need no elaboration other than a recognition of the nature and timing of the various functions of the system. These matters, as well as other operational details, will be considered in the ensuing description of the operation.

Operationally considered, it again is noted that one distinct advantage of the present system is its full automation. As long as there are particles avaialable in supply cups 3, the operation is continuous and repetitive. Description of the operation thus can commence at any point which, for present purposes, will be the point at which particles have been deposited in a thin, single-file disposition on the periphery of platen 13. Further, it is assumed that, at this point, the platen has been lowered by the FIG. 3 mechanism and that it is free to rotate. Rotation then commences when platen motor is switched 'on' by its driver 34 responsively to the generation of a signal by generator 33. Preferably, the program instructions trigger the generator in a timed sequence with the lowering of the platen and rotation continues until motor 24 is switched 'off' by another signal. This 'off' signal occurs only when a particle has been rotated into a position in which it is wholly within the frame viewing area of the optics. If, for example, the particle extends partially beyond this frame, no signal is generated and platen rotation continues. Thus, the generation of the 'off' signal is a feed-back from the scan of the particle as it is applied in digitized video from to the computer. The next result of this type of rotational control is that particles not deposited precisely on the platen will not be analyzed. As will be appreciated, such a result places considerable importance upon the precision of the particle feeding and handling mechanisms including distributor cone 12, sizing plate 14 and the raising and lowering functions of the platen during feed.

With platen rotation arrested and a particle in position to be analyzed, the next step which, again, is controlled by the computer program, is to focus the optics on the particle. Here again, it will be appreciated that each particle brought into the viewing area will not be in precisely the same position and that a detailed examination of it will depend upon a focussing operation obtained by moving the objective lens of the microscope a small distance. Focussing motor 19 provides the necessary drive and, again, it is responsive to a signal derived from generator 33. In practice, this signal also is a feed-back from the scan. In other words, the particle is viewed and the focus motor driven responsively to the video an amount capable of producing the focus which amount again is determined by the viewing. It is to be noted that the focus motor drive shaft is the same shaft used to raise and lower the platen. However, interference between these two drives is avoided by assuring that, when the platen is in its 'down' position, screw 23 is lowered out of contact with the plate. The small movement needed for the focussing takes place with the screw out of contact with the platen.

The particle being in focus, its examination then can be conducted. As noted, this examination includes the different views obtained by rotatably indexing mirror wheel 41. In the examination the computer is programmed to scan a large number of points on the TV scan and these points may be the same for each view. Thus, the program may conduct the examination for the top view following which it generates a signal causing mirror motor 18 to rotate wheel 41 sufficiently to produce the rear view of FIG. 7. Successive front and bottom views are obtained in the same manner.

Upon completion of the scan for a single particle, the computer then produces another signal switching platen motor to 'on' and causing the platen to rotate sufficiently to bring another particle into the viewing area where it is stopped and the foregoing operations repeated. In this manner all of the particles lined up properly on the periphery of the platen will be examined. When this has been accomplished, it is necessary to remove all particles from the platen so that a new supply can be fed to it. Blower 36 is used for this removal or cleaning operation.

Operation of the blower again in controlled by the computer which may be programmed to initiate a signal upon a full 360° rotation of the platen. The signal is applied through a driver to switch blower motor and produces the necessary air blast. It, of course, also is possible to operate the blower responsively to some other switching mechanism capable of detecting the 360° rotation or whatever degree of rotation is selected. In the foraminafera study, no special effort was made to select and preserve particular shells. In other operations, a sorting procedure may be desired in which certain particles are discarded and the others kept. If desired, the system can include some means, such as a suction devic, which draws off selected particles into one receptacle. The others then will be blown into another receptacle so that, for example, defective particles are separated from the quality ones. The separation again would be controlled by the scan.

After the platen has been cleaned, the new supply is delivered by the conveyor. A signal synchronized with the blower signal initiates sample motor 2 to produce the previously-described stepped action resulting in the spilling of a measured amount of particles from a conveyor cup onto the apex of distributor cone 12. However, prior to this feed, platen 13 is moved upwardly into contact with sizing plate 14 so as to block flow from feed aperature 17. The movement is produced by focus motor 19 in the manner already described. Since the same drive shaft used for raising the platen is used for the focussing, both actions are controlled by one driver or switch 34. The final step, which completes the described operation, is the lowering of the platen to cause the particles to drop onto it in position to be rotatably carried to the viewing area.

The present system has a number of advantages which, apparently, have not previously been available. First, it permits a fully automated and closely synchronized examination in detail of various types of particulate matter. The detail is achieved by assuring the proper positioning of the particles on the platen and then by stopping each properly-positioned particle for examination. The use of the distributor cone, the sizing plate and the platen manipulation are important considerations in achieving these results. Also, because the examination is made of a stationary particle, its characteristics can be fully examined by viewing it from the top, front, rear, bottom, etc. Depending upon the type of scan used, a computer examination can be obtained for various characteristics including morphology, size, shape, texture, translucency, color and, if desired, composition. As to composition, known scanning devices such as X-ray and electron beams can be employed to provide information relative to internal structure and density, as well as chemical composition. Such alternate scanning can be employed either in an ancillary manner with the optics or, in some situations, used as a substitute for the optics.

A further advantage is that the system is capable of unattended, efficient operation for long periods of time. For example, the described implementation has operated up to 14 hours and can look at about 2400 shells without human intervention. Its speed of operation is reasonably fast considering the fact that it scans a relatively large number of points in the TV frame. It is not intended to comparable in speed to commercial sorters in which the material is examined in a flowing or moving condition. However, for operations in which relatively sophisticated detail is needed, the computer-controlled operation and the computer analyses of each particle achieves an excellent handling rate capable of providing a large amount of information in a relatively short period of time.

Obviously many modifications and variations of the present invention are possible in the light of the above teachings. It is therefore to be understood that within the scope of the appended claims the invention may be practiced otherwise than as specifically described.

I claim:

1. An automated system for analyzing particulate matter comprising:
   a supply of said particulate matter,
   a horizontally-disposed wheel-like platen,
   means for feeding a portion of said supply particles to said platen,
   means for distributing said portion in a single-file arrangement on the peripheral edge portion of the platen,
   means for rotatably driving said platen,
   means for scanning a frame area of said peripheral edge and for generating an electrical scan output, said scanned frame area being fixed relative to platen rotation, and
   signal generating means operatively coupled to said scanned output and having an output coupled to said platen drive, said generating means being operatively responsive to said scanned output for stopping said platen rotation when one of said particles is within said frame area whereupon a stationary particle is sequentially viewed and for resuming said rotation upon completion of said sequentially viewing whereupon another particle is carried into said frame area for viewing.

2. The system of claim 1 further including:
   means coupling said signal generating means to said feeding means for controlling said feed, and
   platen-cleaning means synchronized with said feeding means for periodically removing particles from the platen to permit the feeding of another supply portion.

3. The system of claim 2 wherein said cleaning means is coupled to said signal-generating means whereby the removal occurs periodically.

4. The system of claim 2 wherein said distributing means includes:
   a cone-like member having an apex disposed to receive and divide said particle feed for promoting said single-file distribution on said platen.

5. The system of claim 4 wherein said distributing means further includes a sizing plate, and
   said system also includes a stationary frame structure having a particle containment wall member extending upwardly of said horizontal platen around and in close proximity to its peripheral edge,
   said sizing plate being a ring-shaped member detachably carried by said frame structure in position for receiving particles directly from the cone and guiding them onto the platen; the lower portion of the plate being dimensioned to provide a predetermined feed-aperature spacing between its outer peripheral edge and the inner periphery of said containment wall member with said spacing being as small as possible relative to the size of the supply particles for improving said single file platen distribution and minimizing the frame area to be scanned.

6. The system of claim 5 further including:
   means for moving said platen up and down into and out of contact with said sizing plate, and
   means coupling said signal generating means to said platen-moving means whereby the platen can be moved up and down and said movement being synchronized with said operation of said feeding means.

7. The system of claim 4 wherein said feeding means includes:
   an endless conveyor belt,
   a series of particle supply cups carried by the belt and formed each with an outwardly-flared lip portion, and
   drive means for advancing said belt and cups in stepped increments,
   the path of travel of said belt including a loop around which each cup travels for moving the cup from an upright to upside-down position, said incremental belt drive producing an incrementally-progressive degree of tilting of the cup with each increment causing a limited portion of said cup particles to spill over said flared lip portion onto said cone apex.

8. The system of claim 1 wherein said scanning means is an optical means focused on said frame area and including:
   a plurality of relatively movable reflecting members disposed to cooperatively provide different views of said frame area and of a particle within said area successively as said reflecting members are moved relatively into different positions.

9. The system of claim 8 wherein said optical scanning means includes:
    a rotatably-driven wheel,
    a first plurality of reflecting members mounted on the wheel for rotation with it,
    drive means for rotating said wheel, and
    a second plurality of relatively stationary reflecting members,
    the relative dispositions of all of said reflecting members being such that successively different views of a frame area particle are optically viewed as said first plurality of reflecting members is rotatably moved into successively different positions relative to said second plurality.

10. The system of claim 9 wherein said platen is transparent and said reflecting members include particular reflecting members for viewing the bottom of a frame area particle through said transparent platen.

11. The system of claim 9 further including:
    means coupling said signal generator to said rotatable wheel drive means whereby the rotation of said wheel is responsive to said signal generator input to permit said optical viewing of successively different views of a frame area particle.

12. The system of claim 11 wherein said optical scanning means further includes:
    a microscope focussed on said frame area for providing an image of said framed particle,
    TV camera means focussed on said imcroscope image and generating an analogue electrical output of the image, and
    digitizer means coupled to said analogue output for providing a digital feedback signal to said signal operating means.

13. The system of claim 12 further including:
    drive means for focussing said microscope on a framed particle, and
    means coupling said focussing drive means to said signal generator means whereby said focussing operation is responsive to said digital feedback signal.

14. The system of claim 13 further including:
    means for raising and lowering said platen to improve said particle feeding and distribution operations, and
    means coupling said platen-moving means to said focussing drive means whereby said platen movements are responsive to said signal generator means.

* * * * *